United States Patent
Craven et al.

(10) Patent No.: US 9,486,152 B2
(45) Date of Patent: Nov. 8, 2016

(54) RESPIRATORY-BASED CONTROL OF MEDICAL PROCEDURE

(75) Inventors: Michael W. Craven, Roseville, MN (US); Timothy R. Jarvis, Minneapolis, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 2874 days.

(21) Appl. No.: 11/924,989

(22) Filed: Oct. 26, 2007

(65) Prior Publication Data

US 2008/0221459 A1   Sep. 11, 2008

Related U.S. Application Data

(60) Provisional application No. 60/894,045, filed on Mar. 9, 2007.

(51) Int. Cl.
- *A61B 5/08* (2006.01)
- *A61B 5/042* (2006.01)
- *A61B 5/06* (2006.01)
- *A61B 5/00* (2006.01)

(52) U.S. Cl.
CPC ............... *A61B 5/0422* (2013.01); *A61B 5/06* (2013.01); *A61B 5/08* (2013.01); *A61B 5/721* (2013.01)

(58) Field of Classification Search
USPC ....... 600/424, 481, 483, 484, 529–543, 547, 600/508, 509; 607/1–9
See application file for complete search history.

(56) References Cited

U.S. PATENT DOCUMENTS

| | | | |
|---|---|---|---|
| 5,540,732 A * | 7/1996 | Testerman | 607/42 |
| 6,454,719 B1 | 9/2002 | Greenhut | |
| 6,956,572 B2 | 10/2005 | Zaleski | |
| 7,187,954 B2 | 3/2007 | Khoury | |
| 2003/0214409 A1 | 11/2003 | Hickle | |
| 2004/0254437 A1 * | 12/2004 | Hauck et al. | 600/374 |
| 2005/0065567 A1 * | 3/2005 | Lee et al. | 607/17 |
| 2005/0115561 A1 | 6/2005 | Stahmann | |
| 2006/0200009 A1 * | 9/2006 | Wekell et al. | 600/300 |

FOREIGN PATENT DOCUMENTS

| | | |
|---|---|---|
| EP | 0429190 | 5/1991 |
| WO | 98/11840 | 3/1998 |

OTHER PUBLICATIONS

PCT International Search Report and Written Opinion of the International Searching Authority for PCT/US08/55957 dated Aug. 15, 2008.

* cited by examiner

*Primary Examiner* — Christian Jang
*Assistant Examiner* — Michael Catina
(74) *Attorney, Agent, or Firm* — Wiley Rein LLP

(57) ABSTRACT

A medical system (100) is disclosed that provides a respiratory-based control of at least one medical procedure. In this regard, the medical system (100) includes one or more appropriate sensors (108) for providing respiratory data on a patient (104). This respiratory data is utilized by respiration assessment logic (116) to determine if the respiratory data has exceeded one or more respiration thresholds and which may be equated with a "sudden" respiratory event. Identification of such a sudden respiratory event by the logic (116) results in the suspension of the noted medical procedure. Patient respiration data may also be displayed, for instance in a color that depends upon its magnitude or level.

23 Claims, 12 Drawing Sheets

RESPIRATORY-BASED CONTROL OF MEDICAL PROCEDURE

CROSS-REFERENCE TO RELATED APPLICATIONS

This application claims the benefit of U.S. provisional application No. 60/894,045, filed 9 Mar. 2007, entitled "Respiratory-based control of medical procedure," which is hereby expressly incorporated by reference as though fully set forth herein.

BACKGROUND OF THE INVENTION a. Field of the Invention

The instant invention is directed toward suspending, modifying, or controlling a medical procedure under certain conditions. More specifically, the instant invention relates to monitoring patient respiratory data and suspending, modifying, or controlling a medical procedure upon encountering an exceedance of at least one respiratory threshold.

b. Background

Cardiac mapping systems such as the Ensite™ Advanced Mapping System by St. Jude Medical, Inc., and the Carto™ Electroanatomical Mapping System by Biosense Webster provide non-fluoroscopic navigation of conventional electrophysiology catheters. The Ensite™ Advanced Mapping System's navigation methodology is based on the principle that when electrical current is applied across two surface electrodes, a voltage gradient is created along the axis between the electrodes. While any number of electrode pairs may be used, typically, six surface electrodes are placed on the body of the patient in three pairs: anterior to posterior, left to right lateral, and superior (neck) to inferior (left leg). The three electrode pairs form three orthogonal axes (X-Y-Z), with the patient's heart being at least generally at the center.

The noted surface electrode pairs are connected to the Ensite™ Advanced Mapping System, which alternately sends an electrical signal through each pair of surface electrodes to create a voltage gradient along each axis, forming a transthoracic electrical field. Conventional electrophysiology catheters may be connected to the Ensite™ Advanced Mapping System and advanced to the patient's heart. As a catheter enters the transthoracic field, each catheter electrode senses voltage, timed to the creation of the gradient along each axis. Using the sensed voltages compared to the voltage gradient on all three axes, EnSite™ NavX™ navigation and visualization technology calculates the three-dimensional position of each catheter electrode. The calculated position for the various electrodes occurs simultaneously and repeats many times per second (e.g., about 93 times per second).

The Ensite™ Advanced Mapping System displays the located electrodes as catheter bodies with real-time navigation. By tracking the position of the various catheters, EnSite™ NavX™ navigation and visualization technology provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired/required.

In accordance with the foregoing, conventional electrophysiology catheter electrodes may be located in EnSite™ NavX™ navigation and visualization technology using a transthoracic impedance of a low-level signature frequency, which is sent and received between surface electrodes on the patient's skin. The calculated catheter electrode positions may be displayed relative to surface electrodes. These catheter electrodes may be used to mark discrete locations within the heart, such as for building models of cardiac chambers, marking discrete sites of diagnosis (mapping), or guiding and marking positions of therapy delivery.

It should be appreciated that during respiration portions of the thoracic cavity move relative to the surface electrodes and volumes may change. Thus, catheter electrodes in the heart move relative to the surface electrodes. Current systems do not account for this movement, and are accordingly creating static labeling of a dynamic model. This can cause errors in location, map generation and display, and treatment.

Current systems can try to correct for this artifactual motion by a respiration compensation functionality that is incorporated into the Ensite™ Advanced Mapping System. A respiration compensation functionality is utilized in the Ensite™ Advanced Mapping System to adjust to respiratory motion from intracardiac catheters by: (1) taking a 12-second data sample of patient respiration, including motion on intracardiac electrodes and impedance changes measured by the EnSite™ NavX™ navigation and visualization technology surface electrodes; and (2) following the collection of such a respiration data sample, the respiration compensation functionality may monitor the surface electrode impedance, and as the impedance changes, the respiration compensation functionality will adaptively compensate for motion artifacts on intracardiac electrode navigation. However, the respiration compensation functionality will only adapt to respiration levels (impedance levels) within the range measured during the sample. Respiration can also cause similar difficulties in systems that do no use surface electrodes.

BRIEF SUMMARY OF THE INVENTION

A first aspect of the present invention is embodied by a medical system that includes at least one sensor (e.g., a first sensor) and what may be characterized as respiration assessment logic. The first sensor may be positioned relative to a patient such that its output provides patient's respiration data. The respiration assessment logic may be operatively interconnected with the first sensor and is configured to identify the existence of a first condition. Although not required by the first aspect, any action or combination of actions may be initiated in response to the identification of a first condition. For instance, at least a first medical procedure may be suspended if the respiration assessment logic identifies an occurrence of the first condition. Another option would be to provide an appropriate notification as to the existence of the first condition if the respiration assessment logic identifies an occurrence of a first condition.

A second aspect of the present invention is embodied by a method for performing a first medical procedure. Patient respiration data is acquired during the execution of the first medical procedure. This patient respiration data may be evaluated in any appropriate manner. If this evaluation identifies the existence of a first condition, further execution of the first medical procedure is suspended, modified, or controlled based on respiration data for at least a certain period of time.

A third aspect of the present invention is embodied by a method for performing a first medical procedure. A first patient respiration data sample is acquired, and that includes at least one complete patient respiration cycle. The first medical procedure may include marking a plurality of physiological locations. Patient respiration data is acquired during the first medical procedure. This patient respiration data may be evaluated in any appropriate manner, but in any case utilizing the first patient respiration data sample in at least some respect. If this evaluation identifies the existence of a first condition, marking procedures are suspended for at least a certain period of time.

A fourth aspect of the present invention is embodied by a system/method that may be used to control a first medical procedure, although control may not be required in all instances. Patient respiration data is acquired. This patient respiration data may be evaluated in any appropriate manner. The patient's respiration level is displayed in a color that depends upon the magnitude of the respiration level. Respiration levels within a first range of any appropriate size are displayed in a first color, while respiration levels within a second range of any appropriate size are displayed in a second color that is different than the first color.

Various refinements and/or additional features that may be utilized in relation to each of the above-noted aspects will now be addressed, and which may be used individually or in any combination. The various features addressed above in relation to each particular aspect also may be utilized in any of the other aspects, individually or in any combination.

The patient respiration data may be in any form, but is preferably reflective of the patient's respiration level. In any case, the first condition may be one that has at least some type of adverse effect on or in relation to the first medical procedure, and which may be identified through assessment of patient respiration data. The first condition may be equated with what may be characterized as a sudden respiratory event. Representative sudden respiratory events include without limitation gasping, sighing, talking, coughing, or snoring.

A number of characterizations may be made in relation to the first condition. One such characterization is that the first condition is representative of a patient respiration that exceeds one or more respiration thresholds. Another such characterization is that the first condition is representative of a patient respiration that is outside of a predetermined respiration range (e.g., having a pair of limits or thresholds). Yet another characterization is that the first condition is representative of a patient respiration that exceeds a baseline respiration by more than a certain, predetermined amount or percentage. One respiration threshold may be associated with the end of inhalation during normal respiration (e.g., within a certain amount of a maximum inhalation value or an average maximum inhalation value identified from an initializing patient respiration data sample), while another respiration threshold may be associated with the end of exhalation during normal respiration (e.g., within a certain amount of a maximum exhalation value or an average maximum exhalation value identified from an initializing patient respiration data sample). Any respiration threshold or respiration range that is utilized in the assessment of patient respiration data may be adjusted at any appropriate time and in any appropriate manner. For instance, each respiration threshold that is utilized could be independently adjustable if desired/required and set at any appropriate level or magnitude. Multiple respiration thresholds could also be simultaneously adjusted.

Patient respiration data may be obtained in any appropriate manner, such as through one or more appropriate sensors (e.g., at least a "first sensor"). Each such sensor may be of any appropriate size, shape, configuration, and/or type, and furthermore may be positioned at any appropriate location on or otherwise relative to the patient. For instance, one or more sensors may be in the form of a patch electrode or the like that is appropriately secured to the skin of the patient at an appropriate location. Multiple sensors may be utilized and disposed in any appropriate arrangement on or otherwise relative to the patient to provide patient respiration data. In one embodiment, impedance is used as a parameter for monitoring the patient's respiration. In this regard, the impedance between a pair of sensors may be determined in any appropriate manner and used in the assessment of the patient respiration data to identify any occurrence of a first condition. Any appropriate parameter or combination of parameters that would be indicative of the patient's respiration (more specifically, the level of respiration) may be used in the patient respiration data assessment (e.g., a transthoracic impedance; at least one electrophysiological parameter; pressure from one or more pressure-sensing catheters; one or more outputs from respiration equipment).

The patient respiration data assessment functionality may be incorporated/implemented in any appropriate manner, such as in software, hardware, or any combination thereof. In any case and in one embodiment, the patient respiration data assessment only evaluates an amplitude of a parameter that relates to the patient's respiration, where this parameter corresponds with or may be derived from/using the output from one or more sensors. For instance, although a parameter that is indicative of the patient's respiration may be conveyed in a waveform, the patient respiration data may simply determine whether any maximum or any minimum of the waveform exceeds a corresponding respiration threshold.

Patient respiration data may be displayed in any appropriate manner and at any appropriate location (e.g., alongside a navigation display). Any graphical/visual representation of patient respiration data may be presented on an appropriate display. For instance, patient respiration data may be presented on a display as a movable marker or indicator on a respiration meter with a plurality of gradations or caliper lines. Patient respiration data may be presented on this meter as a percentage of a predetermined maximum/minimum patient respiration level or value (e.g., patient respiration data may be appropriately presented on a display in relation to at least one predetermined respiration value). The color of this movable marker or indicator may be dependent upon its position on the meter to in essence provide at least two visual indicators of the patient's respiration (i.e., its physical position on the meter, along with its color). Any appropriate number of visual or other indicators of the patient respiration data may be provided and in any appropriate manner. For instance, in addition to a color change, the movable marker or indicator, or the entire meter or at least a relevant portion thereof, may also flash when the patient respiration data assessment has suspended the first medical procedure. The described patient respiration data assessment described herein may be used with or without respiration compensation functionality. In the former regard, the gradations of the respiration meter that correspond with respiration levels where respiration compensation functionality is provided or available may be displayed in a different color than respiration levels outside of this respiration compensation zone.

The first condition again may be when a patient's respiration is outside of a predetermined respiration range or above/below a certain respiration threshold. Patient respiration data that falls within a first portion of a predetermined respiration range may be presented in a first color on a display (e.g., within 0% to 75% of a certain respiration value or threshold, and which may be equated with a "normal" respiration zone), while patient respiration data that falls within a second portion of a predetermined respiration range may be presented in a second color on a display (e.g., between 75% and 100% of a certain respiration value or threshold, and which may be reflective of a "cautionary" respiration zone that is between the above-noted "normal" respiration zone and what may be characterized as an "unacceptable" respiration zone for purposes of the first medical procedure, where an unacceptable respiration zone may be equated with a first condition). Patient respiration data that falls outside of both the first portion and the second portion of a predetermined respiration range may be presented in a third color on a display (e.g., patient respiration data that is at least 100% of a certain respiration value or threshold, and which may be equated with a first condition). For instance, the color of the movable marker or indicator on the above-noted respiration meter may be utilized for identifying the three respiration level zones or ranges. Any number of ranges or zones could be utilized, with each having its own corresponding color.

The evaluation of the patient respiration data for purposes of identifying each occurrence of a first condition may benefit from an initialization procedure. This initialization procedure may entail acquiring a patient respiration data sample, and thereafter utilizing this patient respiration data sample in at least some fashion in the patient respiration data evaluation. For instance, the patient respiration data sample may be utilized to establish one or more respiration thresholds, a respiration baseline, and/or to establish a predetermined respiration range for the patient respiration data evaluation (e.g., to define a first condition). In one embodiment, the patient respiration data sample includes at least one full respiration cycle that is devoid any of the above-noted types of sudden respiratory events (e.g., gasping, sighing, talking, coughing, snoring). It may be desirable to repeat this initialization procedure during the performance of the first medical procedure, for instance if the patient respiration data is tending toward staying in the above-noted second or cautionary respiration zone.

The first medical procedure may be of any of appropriate type, and may be undertaken by any appropriate component or combination of components (e.g., using one or more endocardial electrodes, such as a catheter electrode or the like). For instance, the first medical procedure may be in the form of marking a physiological location on or within the body of the patient, such as a discrete location within the patient's heart. The first medical procedure may also be in the form of acquiring and/or storing anatomical/physiological location information (e.g., location information of a particular anatomical structure or surface). Representative first medial procedures include without limitation cardiac labeling, cardiac geometry collection, cardiac mapping, cardiac lesion marking, and the like. The first medical procedure also may be an operation associated with an anatomical modeling system of any appropriate type (e.g., acquisition of anatomical/physiological location data, storage of anatomical/physiological location data, or both). That is, each of the various aspects addressed herein may be incorporated and/or otherwise utilized by an anatomical modeling system of any appropriate type, such as electrical-based anatomical modeling system or a magnetics-based anatomical modeling system.

The foregoing and other aspects, features, details, utilities, and advantages of the present invention will be apparent from reading the following description and claims, and from reviewing the accompanying drawings.

DETAILED DESCRIPTION

Figure 1:
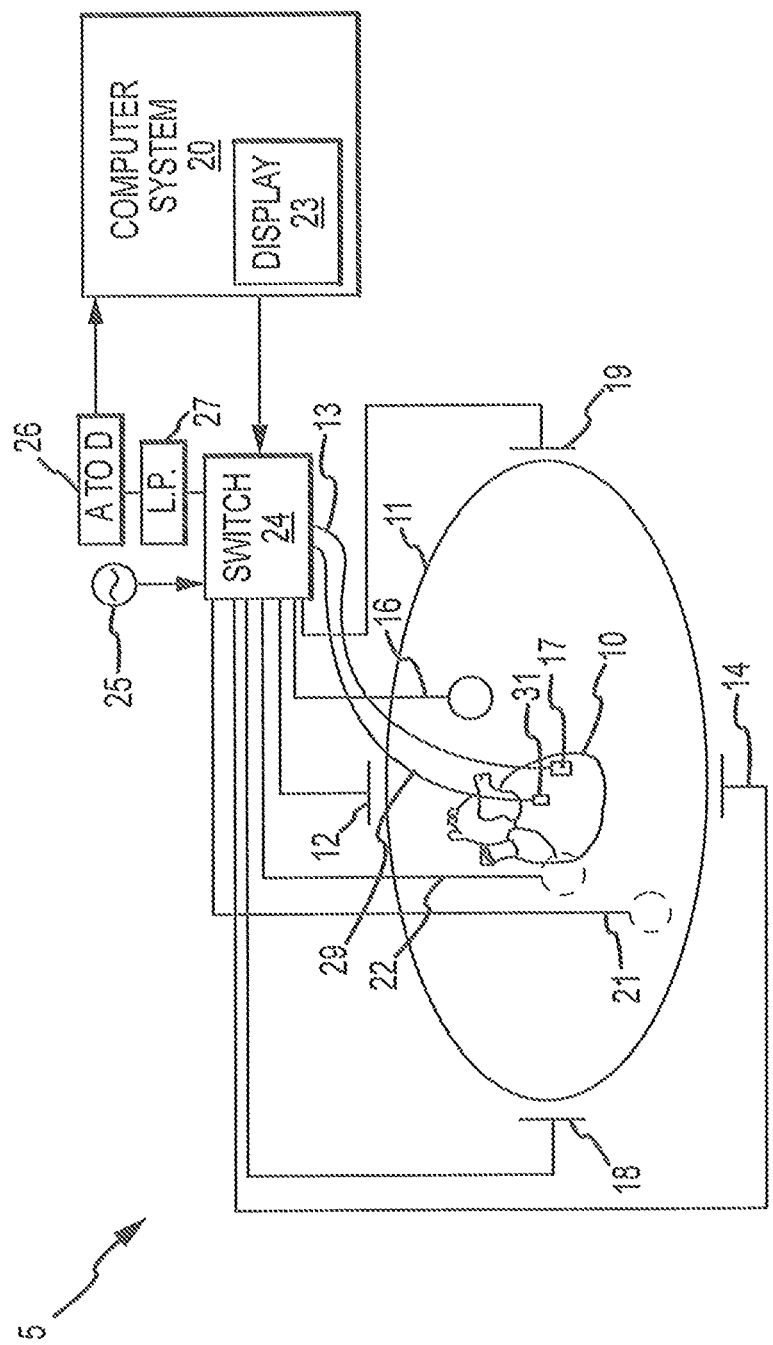
FIG. 1 is a schematic representation of one embodiment of a medical navigation/visualization system.

FIG. 1 presents a schematic of one embodiment of what may be characterized as a medical navigation/visualization system and/or an anatomical modeling system 5. The medical navigation/visualization system 5 will be briefly addressed herein, as it is one such system that may utilize the respiratory-based control functionality that will be addressed in detail below. The medical navigation/visualization system 5 is also discussed in detail in U.S. Pat. No. 7,263,397, that is entitled "METHOD AND APPARATUS FOR CATHETER NAVIGATION AND LOCATION AND MAPPING IN THE HEART," that issued on Aug. 28, 2007 and is assigned to the assignee of this patent application, and the entire disclosure of which is incorporated by reference in its entirety herein.

The patient 11 is only schematically depicted as an oval for clarity. In a preferred embodiment, three sets of surface or patch electrodes are shown as 18, 19 along a Y-axis; as 12, 14 along an X-axis; and 16, 22 along a Z-axis. Patch electrode 16 is shown on the surface closest to the observer, and patch electrode 22 is shown in outline form to show its placement on the back of patient 11. An additional patch electrode, which may be referred to as a "belly" patch, is also seen in the figure as patch electrode 21. Each patch electrode 18, 19, 12, 14, 16, 22, 21 is independently connected to a multiplex switch 24. The heart 10 of patient 11 lies between these various sets of patch electrodes 18, 19, 12, 14, 16, 22. Also seen in this figure is a representative catheter 13 having a single distal electrode 17 for clarity. This distal electrode 17 may be referred to as the "roving electrode" or "measurement electrode" herein. Multiple electrodes on each catheter may be used. A fixed reference electrode 31 attached to a heart wall is also seen in the figure on an independent catheter 29. For calibration purposes, this electrode 31 is known to be stationary on the heart. It should be appreciated that in use the patient 11 will have most or all of the conventional 12 lead ECG system in place as well, and this ECG information is available to the system although not illustrated in the figure.

Each patch electrode 18, 19, 12, 14, 16, 22, 21 is coupled to the switch 24, and pairs of electrodes 18, 19, 12, 14, 16, 22 are selected by software running on computer system 20, which couples these electrodes 18, 19, 12, 14, 16, 22 to the signal generator 25. A pair of electrodes, for example electrodes 18 and 19, may be excited by the signal generator 25 and they generate a field in the body of the patient 11 and the heart 10. During the delivery of the current pulse, the remaining patch electrodes 12, 14, 16, 22 are referenced to the belly patch electrode 21, and the voltages impressed on these remaining electrodes 12, 14, 16, 22 are measured by the analog-to-digital or A-to-D converter 26. Suitable low-pass filtering of the digital data may be subsequently performed in software to remove electronic noise and cardiac motion artifact after suitable low pass filtering in filter 27. In this fashion, the various patch electrodes 18, 19, 12, 14, 16, 22 are divided into driven and non-driven electrode sets. While a pair of electrodes are driven by the signal generator 25, the remaining non-driven electrodes are used as references to synthesize the orthogonal drive axes.

The belly patch electrode 21 is seen in the figure is one alternative to a fixed intra-cardiac electrode 31. In many instances, a coronary sinus electrode or other fixed electrode in the heart 10 can be used as a reference for measuring voltages and displacements. The raw patch voltage data is measured by the A-to-D converter 26 and stored in the computer system 20 under the direction of software. This electrode excitation process occurs rapidly and sequentially as alternate sets of patch electrodes 18, 19, 12, 14, 16, 22 are selected, and the remaining members of the set are used to measure voltages. This collection of voltage measurements may be referred to herein as the "patch data set". The software has access to each individual voltage measurement made at each individual patch electrode 18, 19, 12, 14, 16, 22 during each excitation of each pair of electrodes 18, 19, 12, 14, 16, 22. The raw patch data is used to determine the "raw" location in three spaces (X, Y, Z) of the electrodes inside the heart 10, such as the roving electrode 17.

If the roving electrode 17 is swept around in the heart chamber while the heart 10 is beating, a large number of electrode locations are collected. These data points are taken at all stages of the heartbeat and without regard to the cardiac phase. Since the heart 10 changes shape during contraction, only a small number of the points represent the maximum heart volume. By selecting the most exterior points, it is possible to create a "shell" representing the shape of the heart 10, e.g., at its maximum heart volume. The location attribute of the electrodes within the heart 10 are measured while the electric field is impressed on the heart 10 by the surface patch electrodes 18, 19, 12, 14, 16, 22.

Figure 2:
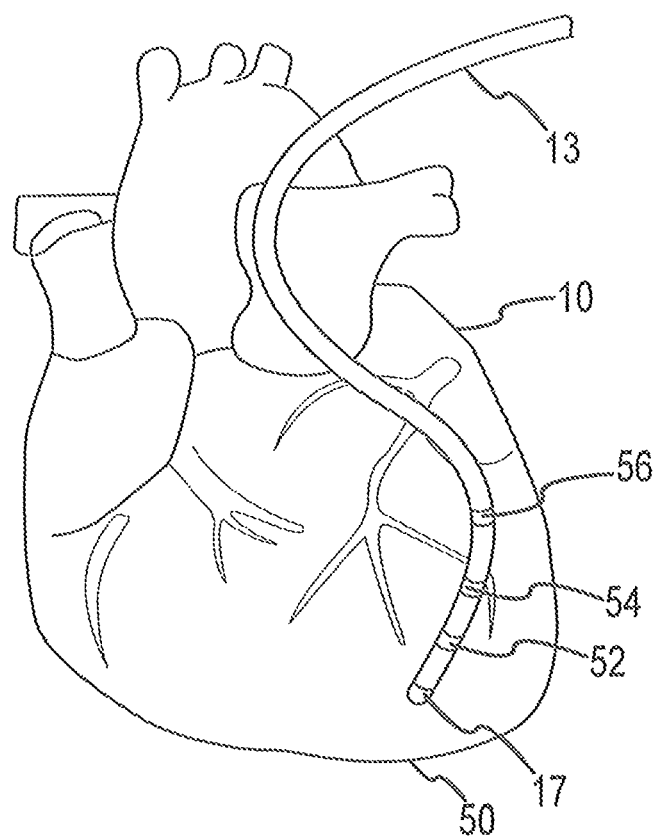
FIG. 2 is a schematic of a catheter in a heart chamber.

FIG. 2 shows a catheter 13, which may be a conventional EP catheter in the heart 10. In the figure, the catheter 13 is shown in the left ventricle 50. The catheter 13 has additional electrodes 52, 54, and 56. Since these electrodes 52, 54, 56 lie in the heart 10, the location process detects their location in the heart 10. While they lie on the surface and when the signal generator 25 is "off", each electrode 18, 19, 12, 14, 16, 22 can be used to measure the voltage on the heart surface. The magnitude of this voltage, as well as the timing relationship of the signal with respect to the heartbeat events, may be measured and presented to the cardiologist through the display 23. The peak-to-peak voltage measured at a particular location on the heart wall is capable of showing areas of diminished conductivity, and which may reflect an infarcted region of the heart 10. The timing relationship data are typically displayed as "isochrones". In essence, regions that receive the depolarization waveform at the same time are shown in the same false color or gray scale.

Figure 3:
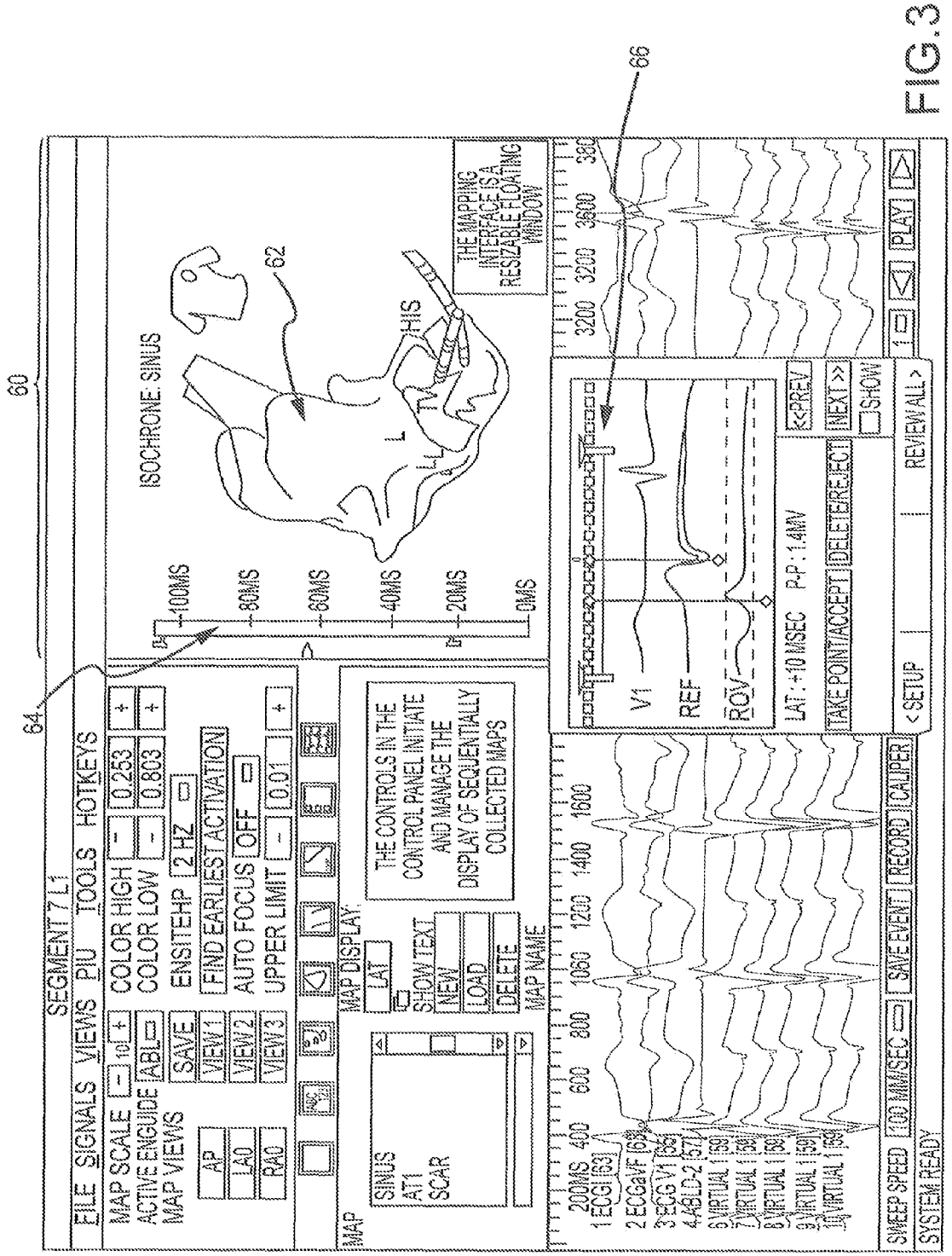
FIG. 3 is a representative output on a display screen used by the medical navigation/visualization system of FIG. 1, showing operation and interaction with the overall system.

FIG. 3 shows an illustrative computer display from the computer system 20 (FIG. 1). The display 23 (FIG. 1) is used to show data to the physician user and to present certain options that allow the user to tailor the system configuration for a particular use. It should be noted that the contents on the display 23 can be easily modified and the specific data presented is only of a representative nature. An image panel 60 shows a geometry of the heart chamber 62 which shows "isochrones" in false color, which is shown in grayscale in the figure with guide bar 64. In this image, the improved location methodology has been used with a roving catheter to create a chamber representation that is displayed as a smoothed contoured image.

The guide bar 64 is graduated in milliseconds and it shows the assignment of time relationship for the false color image in the geometry. The relationship between the false color on the geometry image 62 and the guide bar 64 is defined by interaction with the user in panel 66 as best seen in FIG. 4.

Figure 4:
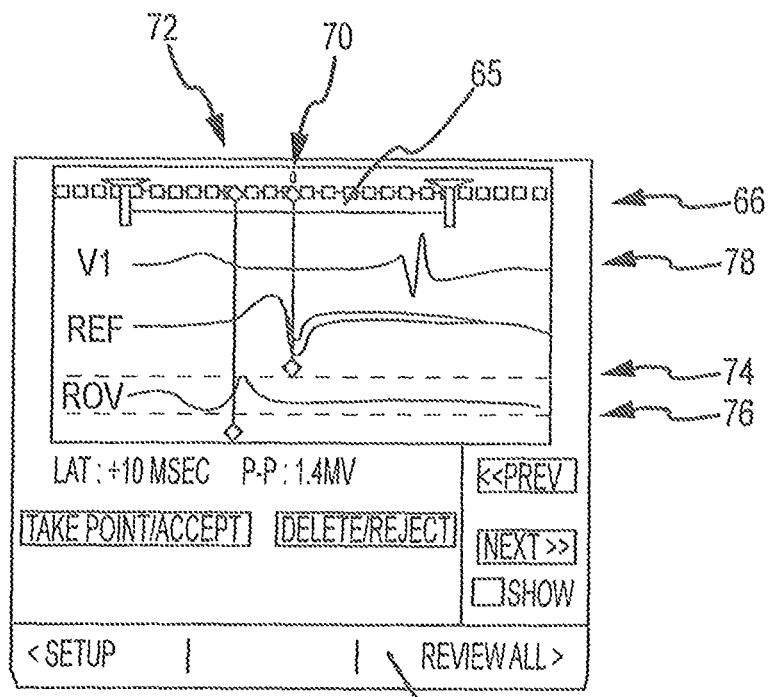
FIG. 4 is a representative output on a display screen used by the medical navigation/visualization system of FIG. 1, showing operation and interaction with a portion of the system.

FIG. 4 is an enlargement of panel 66 of FIG. 3. The panel 66 represents the timing information used to generate the isochrones seen on geometry 62. In general, a fiducial point is selected as the "zero" time. In the figure, the inflection point 70 of a voltage appearing on a reference electrode is used as the primary timing point for the creation of isochrones. This voltage may be acquired from either a virtual reference or a physical reference such as electrode 31 seen in FIG. 1. This voltage tracing in the figure is labeled "REF" on FIG. 4. The roving electrode signal is seen on FIG. 4 and it is labeled "ROV" in the figure. The inflection point of this voltage signal is shown at 72. The color guide bar 65 shows the assignment of color or grayscale tone for the timing relationship seen between inflections 70 and 72.

Also shown on panel 66 of FIG. 4, is the amplitude of the signal present on the roving electrode 17. Note that it lies between two adjustable bands 74 and 76. These bands 74,76 are used to set selection criteria for the peak-to-peak voltage of the signal. In practice, regions of the heart 10 with low peak-to-peak voltage are the result of infarcted tissue, and the ability to convert voltage to grayscale or false color allows identification of the regions that are infarcted or ischemic.

For completeness, in description the tracing 78 labeled "V1" in FIG. 4 is a reference electrode on the surface of the patient 11 in the conventional 12 lead ECG setup. This reference orients the physician to the same events detected on the surface of the patient 11.

Based upon the foregoing, the basic software process proceeds stepwise by first selecting a set of electrodes and then driving them with current pulses. While the current pulses are being delivered, the voltages on several of the other remaining surface electrodes and intracavitary electrodes are measured and stored.

It is this process that collects the various data points associated with multiple endocardial electrode locations. Each point in this set has coordinates in space. In general, several dozen points are collected. A larger data set results in a more complex and higher resolution representation of the heart 10; however, it is computationally more expensive. This raw location data may be corrected for respiration and other artifacts, and then a geometry process is started. In this process, the exterior-most location points in the data are used to create a shape. The surface may be in the form of a convex hull using standard algorithms such as Qhull. This surface is then resampled over a more uniform grid and interpolated to give a reasonably smooth surface stored as a "geometry" for presentation to the physician. Any of the algorithms known in the art may be used to compute the convex hull shape. This hull shape estimates the boundary of the interior of the heart 10 from the set of points. The process can then proceed to resample the convex hull on a regular grid of points in physical space. By resampling the computed hull shape on the regular gird, a larger set of points in generated. Most significantly, this enlarged set of points ensures that computational points are available along the length of each edge of the hull. The next process uses an algorithm for smoothing the convex hull shape. This process forms a mathematically differentiable shape approximating the physiologic shape of the heart chamber. Any of a number of interpolation processes can be adopted to implement this portion of the process. The final process causes the model to exit to a display routine or other process where the computed shape is used for further analysis. This geometry surface is also used as a display surface to present the activation maps. This is also the surface that the EP data is projected on.

As described, the EP catheters are moved over the surface of the heart 10 and while in motion they detect the electrical activation of the heart 10 or EP signals on the surface of the heart 10. During each measurement, the real time location of the catheter electrode is noted, along with the value of the EP voltage or signal. Since this data is not taken with the location data used to create the geometry, a projection process is used to place the electrical information on the nearest heart surfaces represented by the geometry. One implementation is to select two close points or locations in the EP data set and to "drop" a point perpendicular to the "nearest" surface point on the geometric surface. This new point is used as the "location" for the presentation of EP data in the images presented to the physician.

The above-noted surface or patch electrodes 12, 14, 16, 22, 18, 19 used by navigation/visualization system 5 of FIG. 1 may also be used to provide patient respiration data for respiratory-based control of a medical procedure using a transthoracic impedance (e.g., by using a low-level signature frequency, which is sent and received between various of the patch electrodes 12, 14, 16, 22, 18, 19). Generally, an appropriate signal may be sent to a particular one of the patch electrodes 12, 14, 16, 22, 18, 19, and a signal corresponding with the output of one or more of the other patch electrodes 12, 14, 16, 22, 18, 19 may be provided for assessment in relation to what may be characterized as a first condition, where patient respiration data (e.g., a respiration level) exceeds one or more patient respiration thresholds. Identification of the first condition may then be used to suspend at least one medical procedure.

Impedance is one parameter that is reflective of the patient's respiration and that may be used for the above-noted first condition assessment. Other examples, depending on the mapping system or equipment used, could include magnetics, coupling distance, and motion. The impedance changes during a patient's respiratory cycle are based upon the patient's respiratory level. For instance, the amount of air in the patient's lungs has an effect on the impedance. The resistively of the patient's blood also changes during the patient's respiratory cycle and thereby has an effect on the impedance. Impedance data regarding the patient's respiration may be acquired/determined in any appropriate manner, for instance via the output from one or more of the above-noted patch electrodes 12, 14, 16, 22, 18, 19. As the amount of air in the lungs changes, the measured impedance between the electrodes will change. This change is recorded as impedance data. This impedance data may be assessed to identify the respiratory stage, or correlate with a respiratory stage, and be analyzed. This analysis will identify any occurrence of a first condition, and is used to then responsively suspend at least one medical procedure.

Figure 5:
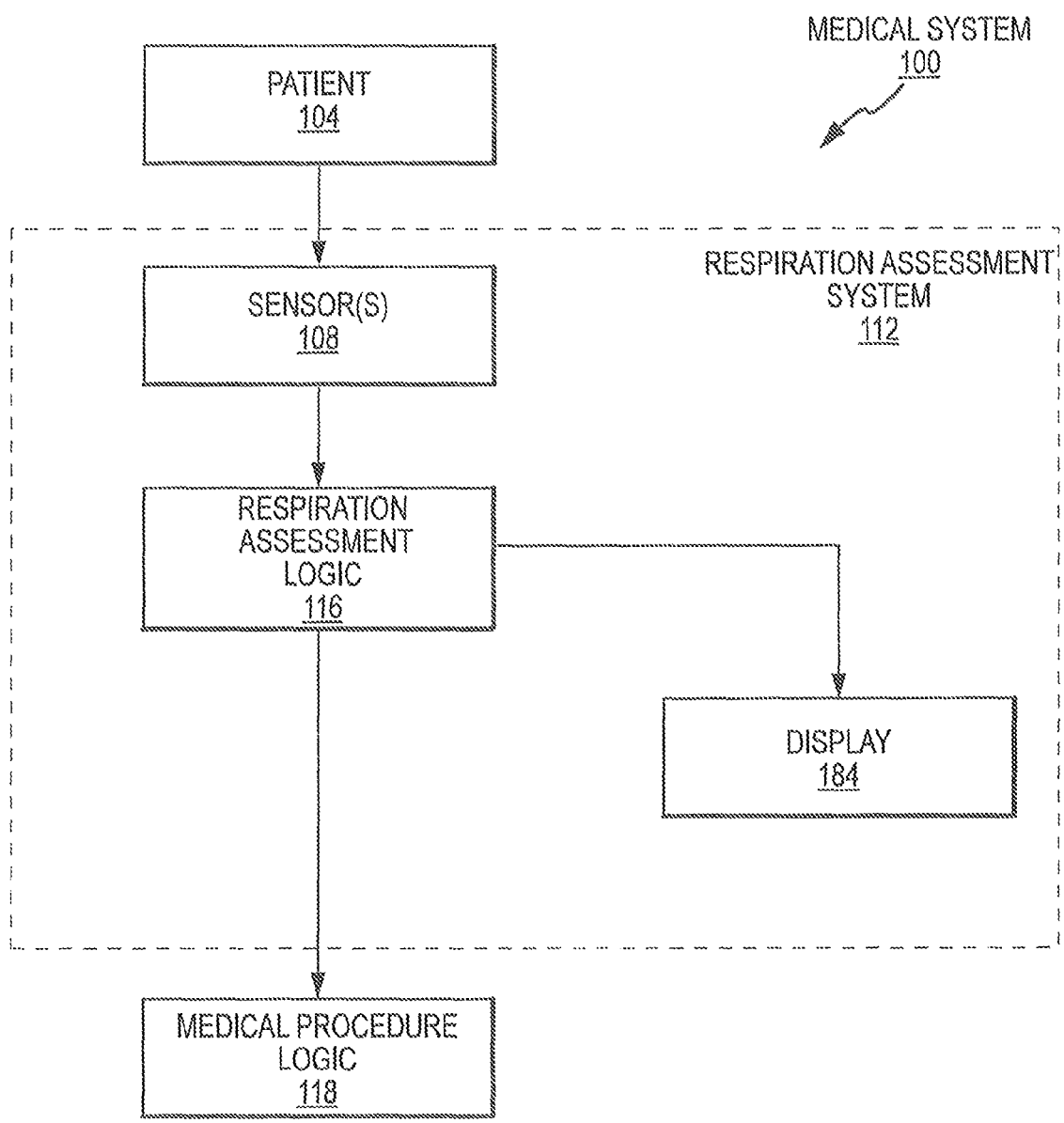
FIG. 5 is a schematic of a medical system that utilizes respiratory-based control of a medical procedure.

One embodiment of a medical system that utilizes respiratory-based control is schematically presented in FIG. 5 and is identified by reference numeral 100. The medical system 100 generally includes a respiration assessment system 112 and medical procedure logic 118. Generally, the respiration assessment system 112 may be incorporated and/or utilized by any appropriate medical system, such as an anatomical modeling system of any appropriate type (e.g., electrical-based; magnetics-based). The medical procedure logic 118 may provide any functionality or combination of functionalities (e.g. to control at least one medical procedure in at least some respect), and furthermore may be associated with any component or combination of components, such as the navigation/visualization system 5 of FIG. 1 or any anatomical modeling system of any appropriate type. For instance, the respiration assessment system 112 may be used to suspend the acquisition and/or storage of location information on an anatomical/physiological surface/structure.

The respiration assessment system 112 includes respiration assessment logic 116 that is operatively interconnected with the medical procedure logic 118, and may be characterized as further including at least one sensor 108 that is associated with a patient 104, along with a display 184. Each sensor 108 and the display 184 may also be part of and/or used by one or more other parts of the medical system 100, such as the navigation/visualization system 5 of FIG. 1.

Each sensor 108 used by the medical system 100 of FIG. 5 may be of any appropriate size, shape, configuration and/or type, and furthermore may be positioned at any appropriate location on or relative to the patient 104. For instance, one or more of the sensors 108 may be in the form of the surface or patch electrodes 12, 14, 16, 22, 18, 19 used by the navigation/visualization system 5 of FIG. 1, and which would be appropriately attached at an appropriate location on the skin of the patient 104 (e.g., in the above-noted arrangement). The output from one or more of these sensors 108 may be utilized by the respiration assessment system 112 to provide respiratory-based control of at least one medical procedure. That is, data provided by one or more of these sensors 108 should be in the form of patient respiratory data or data that is reflective of the patient's respiratory cycle (e.g., data that reflects the changes in the patient's respiratory level during the respiratory cycle).

Data provided by one or more of these sensors 108 is used by the respiration assessment system 112 to provide a respiratory-based control of one or more medical procedures, for instance by communication between the respiration assessment logic 116 and the medical procedure logic 118. This respiration assessment logic 116, along with the medical procedure logic 118 for that matter, may be incorporated/implemented in any appropriate manner, such as in software, hardware, or any combination thereof, and may be disposed at any appropriate location (e.g., the respiration assessment logic 116 and medical procedure logic 118 need not be co-located, although such may be the case).

Figure 6:
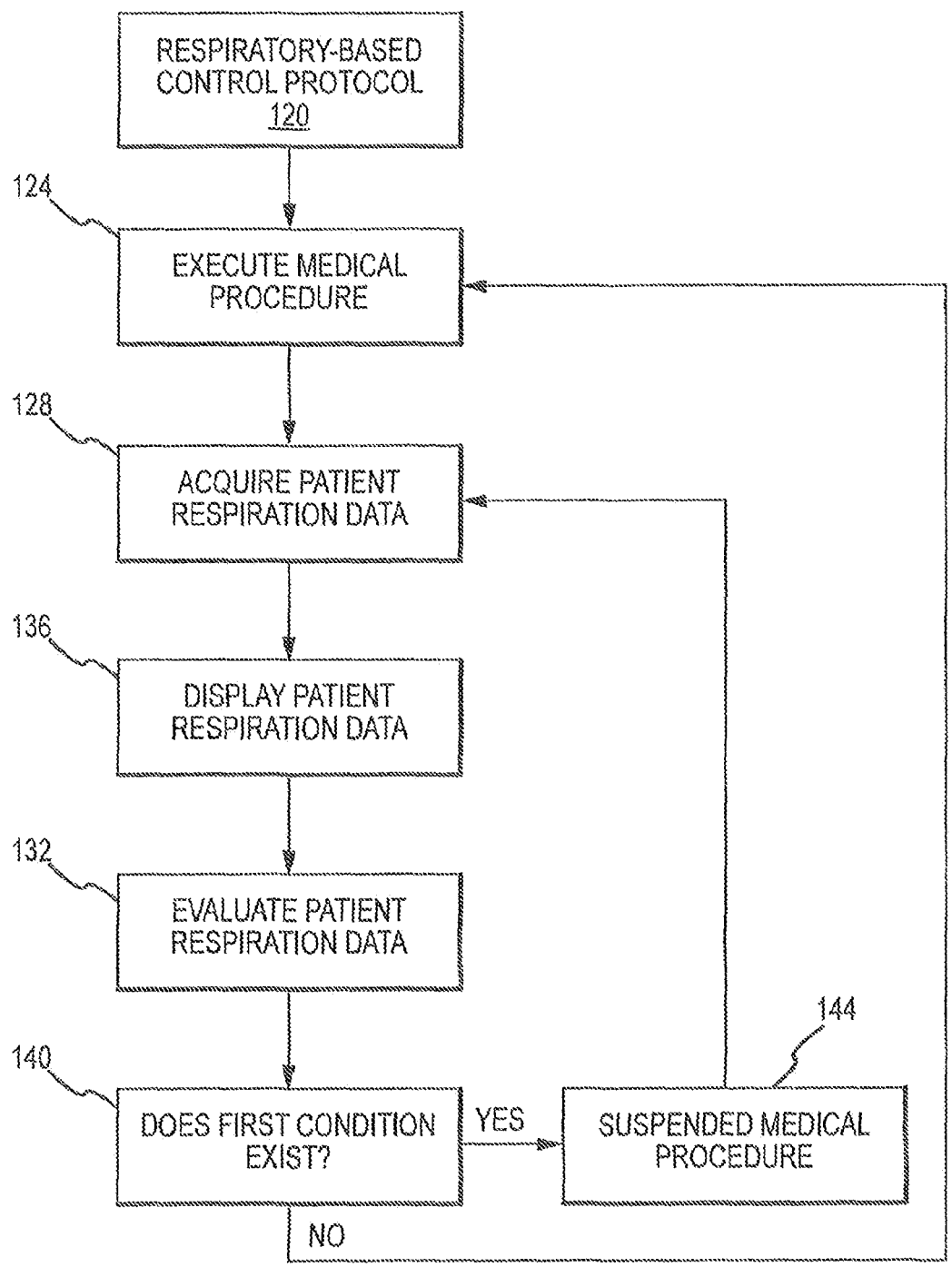
FIG. 6 is a flow chart of one embodiment of a respiratory-based control protocol that may be utilized by the respiration assessment logic from the medical system of FIG. 5.

One embodiment of a respiratory-based control protocol that may be utilized by the respiration assessment logic 116 (FIG. 5) is illustrated in FIG. 6 and is identified by reference numeral 120. Step 124 of the respiratory-based control protocol 120 is directed to executing a medical procedure, such as through the medical procedure logic 118 (FIG. 5). This medical procedure may be of any appropriate type, may be undertaken by any appropriate component or combination of components (e.g., using one or more endocardial electrodes, such as a catheter electrode or the like), and may be undertaken on any basis (e.g., the medical procedure may be performed continuously over a certain period of time; the medical procedure may be performed at one or more times over a certain period of time). In the context of the navigation/visualization system 5 of FIG. 1, the medical procedure associated with step 124 of the respiratory-based control protocol 120 of FIG. 6 may be characterized as marking a physiological location on or within the body of the patient 104 (FIG. 5), such as a discrete location within the heart of the patient 104, acquiring and/or storing physiological location information, or the like. Representative medical procedures for step 124 of the respiratory-based control protocol 120 of FIG. 6 include without limitation cardiac labeling, cardiac geometry collection, cardiac mapping, cardiac lesion marking, and the like.

Patient respiration data is acquired through execution of step 128 of the respiratory-based control protocol 120. Patient respiration data may be acquired on any timing basis (e.g., on a real-time basis; in accordance with any algorithm), but is preferably acquired throughout the medical procedure associated with step 124. It also may be desirable to acquire a patient respiration data sample before the medical procedure associated with step 124 is initiated and as will be discussed in more detail below in relation to the initialization protocol 148 of FIG. 7. Any data that is representative of the patient's respiration (e.g., respiration level) may be acquired through execution of step 128 of the protocol 120, so long as this data may be assessed to determine if a first condition exists. Impedance data is one such parameter as noted above. Impedance may be more generally characterized as electrophysiological data. Other electrophysiological data/parameters may be appropriate for providing a first condition assessment. Other parameters on which a first condition assessment could be based include without limitation pressure data from one or more pressure-sensing catheters or other appropriate pressure sensors, one or more outputs from respiration equipment, and magnetic data, e.g., magnetic location data.

The patient respiration data acquired through step 128 of the respiratory-based protocol 120 may be displayed through execution of step 136 of the protocol 120, but in any case is evaluated through execution of step 132 of the protocol 120. This evaluation may be undertaken in any appropriate manner. Preferably, all patient respiration data is evaluated through step 132, although such may not be required in all instances, and preferably this evaluation occurs on a real-time basis or at least with some reasonable degree of frequency. The patient respiration data evaluation associated with step 132 may be characterized as determining if the patient's respiration exceeds one or more respiration thresholds, if the patient's respiration is outside of a predetermined respiration range (e.g., having a pair of limits or thresholds), or if the patient's respiration exceeds a baseline respiration value by more than a certain, predetermined amount (e.g., on a percentage basis or an absolute basis). Such an occurrence may be characterized as a "sudden" respiratory event (e.g., gasping, sighing, talking, coughing, and snoring). A sudden respiratory event may adversely affect the medial procedure associated with step 124 in at least some manner. Accordingly it is desirable to identify these "sudden" respiratory events and adjust the procedure accordingly.

The respiratory-based control protocol 120 generalizes the above-noted sudden respiratory event as one type of a "first condition" in its step 140. If a first condition exists, the medical procedure of step 124 may be suspended in any appropriate manner via step 144 of the protocol 120. Patient respiration data continues to be acquired and evaluated through steps 128 and 132 during any suspension of the medical procedure, but now for purposes of determining if the first condition no longer exists. Once the first condition no longer exists, the medical procedure may be re-initiated in any appropriate manner, such as through another execution of step 124 of the protocol 120. The medical procedure could be resumed on any appropriate basis (e.g., a certain amount of time after a first condition has been identified).

Figure 7:
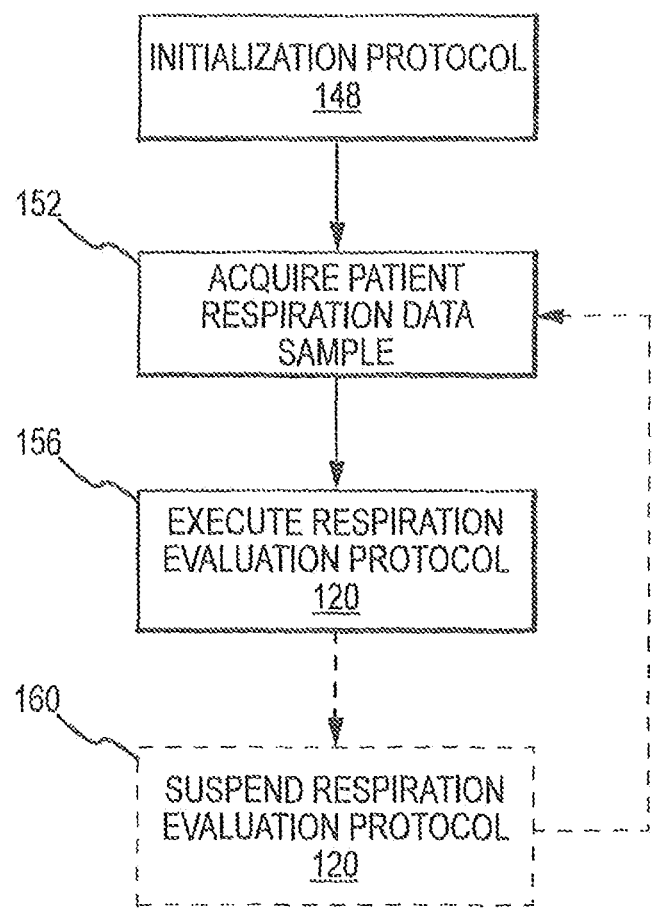
FIG. 7 is a flow chart of one embodiment of an initialization protocol that may be utilized by the respiratory-based control protocol of FIG. 6.
Figure 8:
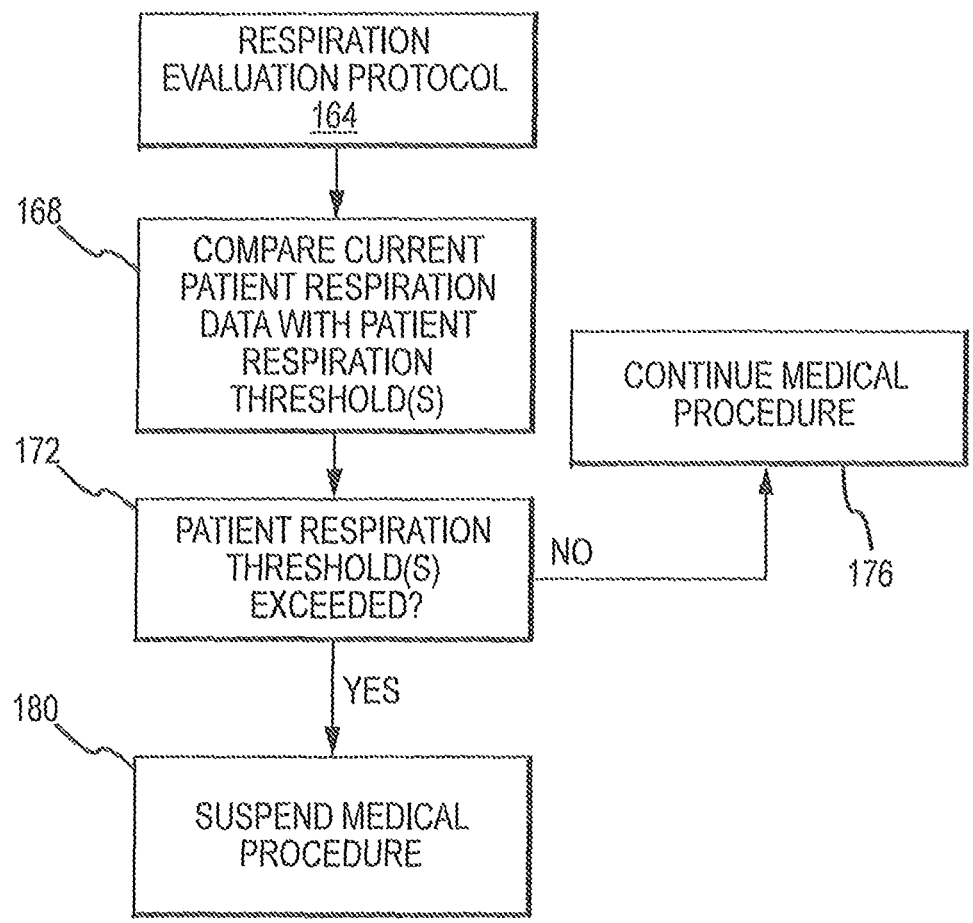
FIG. 8 is a flow chart of one embodiment of a respiration evaluation protocol that may be utilized by the respiratory-based control protocol of FIG. 6.
Figure 9:
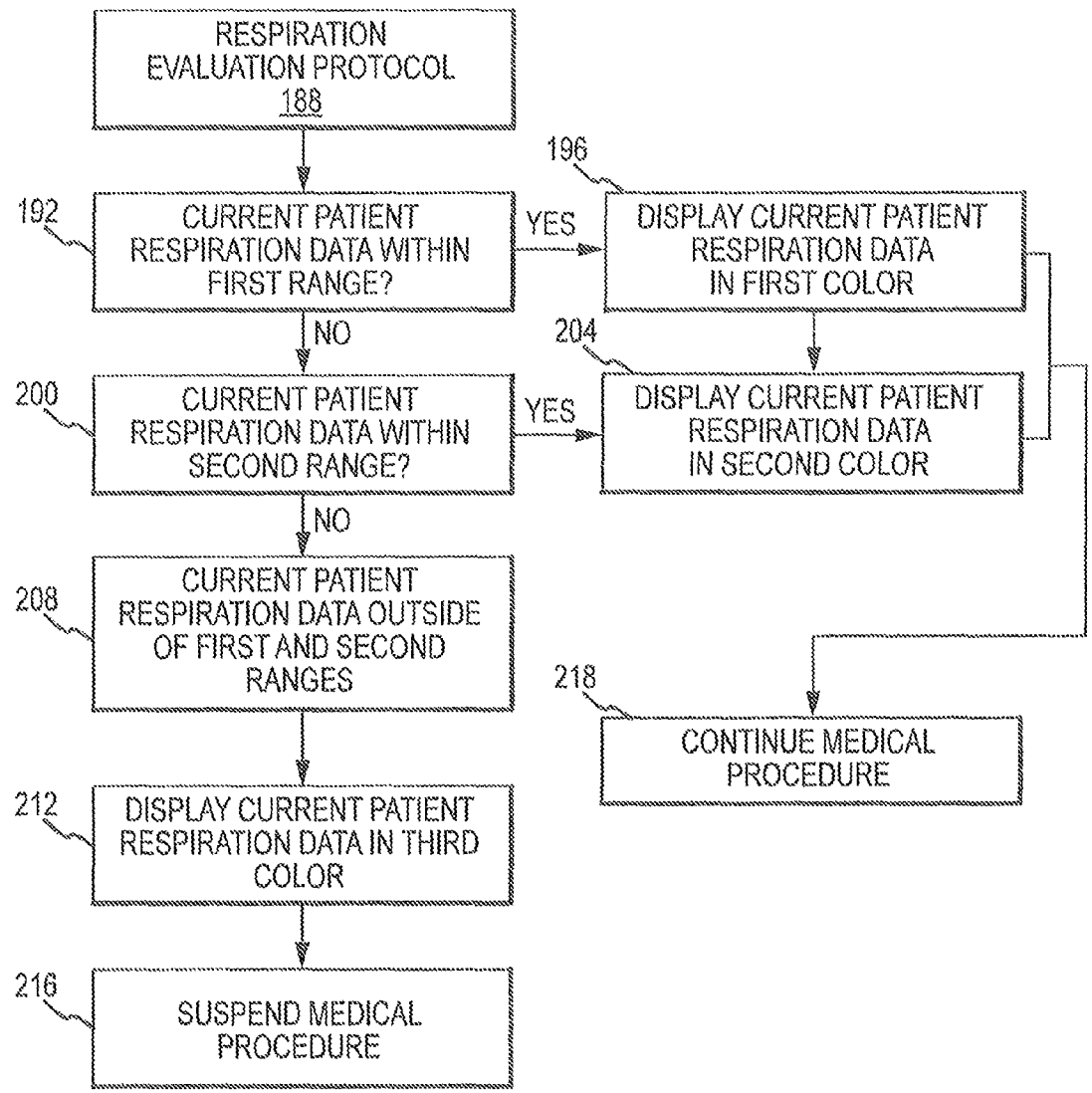
FIG. 9 is a flow chart of another embodiment of a patient respiration evaluation protocol that may be utilized by the respiratory-based control protocol of FIG. 6.

Various additional features may be utilized by the respiratory-based control protocol 120 of FIG. 6, such as the initialization protocol 148 of FIG. 7, the respiration evaluation protocol 164 of FIG. 8, and the respiration evaluation protocol 188 of FIG. 9. Each of these protocols will now be addressed.

The respiratory-based control protocol 120 of FIG. 6 evaluates patient respiration data to identify any occurrence of a first condition for purposes of suspending at least one medical procedure during the existence of this first condition. One way in which patient respiration data may be evaluated for this purpose is to compare the same to one or more respiration thresholds. The initialization protocol 148 of FIG. 7 may be utilized to identify one or more respiration thresholds that are appropriate for the patient 104 (FIG. 5). In this regard, an appropriate patient respiration data sample is acquired through execution of step 152 of the initialization protocol 148. Preferably this patient respiration data sample includes at least one complete respiratory cycle (at least one inhalation and one exhalation) and does not include any of the above-noted type of "sudden" respiratory events. In one embodiment, patient respiratory data is acquired for at least about 10 or 12 seconds to provide such a data sample. Although a respiration threshold may be established in any appropriate manner through a review/analysis of this patient respiration data sample, in one embodiment the maximum and minimum amplitudes of a waveform of the patient respiration data may be calculated or otherwise determined (e.g., respiration baselines), and thereafter may be used to define a maximum respiration threshold (e.g., +100% in FIGS. 10A-C to be discussed below) and a minimum respiration threshold (e.g., −100% in FIGS. 10A-C to be discussed below). Therefore, the current patient respiration data may be visually presented as a percentage in relation to maximum and minimum respiration threshold values and as will be addressed below in relation to the respiration evaluation protocol 188 of FIG. 9 and where representative display outputs are presented in FIGS. 10A-C.

Once an appropriate patient respiration data sample has been obtained through execution of step 152 of the initialization protocol 148, the respiration evaluation protocol 120 of FIG. 6 may be executed in any appropriate manner (e.g., through execution of step 156 of the initialization protocol 148 of FIG. 7). There may be a desire/need to reestablish one or more of the respiration thresholds for purposes of the respiratory-based control protocol 120. In this regard, step 160 of the initialization protocol 148 indicates that the respiratory-based control protocol 120 may be suspended for a repetition of step 152 of the initialization protocol 148 and its acquisition of another patient respiration data sample. Since it may not be required to acquire two or more patient respiration data samples for purposes of the respiratory-based control protocol 120, step 160 of the initialization protocol 140 may be of an optional nature and as indicated by the dashed lines in FIG. 7.

Patient respiration data may be evaluated in any appropriate manner for purposes of the respiratory-based control protocol 120 of FIG. 6. One embodiment of a respiration evaluation protocol that may be utilized by the protocol 120 of FIG. 6 to execute the patient respiration data evaluation is illustrated in FIG. 8 and is identified by reference numeral 164. Step 168 of the protocol 164 of FIG. 8 may replace step 132 of the protocol 120 of FIG. 6, while step 172 of the protocol 164 of FIG. 8 may replace step 140 of the protocol 120 of FIG. 6. Step 168 of the respiration evaluation protocol 164 of FIG. 8 provides a comparison of the patient respiration data with at least one respiration threshold. This comparison may be provided in any appropriate manner (e.g., using an appropriate comparator). If the patient respiration data currently being evaluated in accordance with step 168 of the respiration evaluation protocol 164 does not exceed any respiration threshold being utilized and which is determined through step 172, the respiration evaluation protocol 164 allows for a continuance of the medical procedure (e.g., through step 176). Otherwise, the respiration evaluation protocol 164 proceeds to step 180 and which results in or otherwise accommodates a suspension of the medical procedure through execution of step 180. This suspension of the medical procedure may be initiated in any appropriate manner (e.g., automatically, manually). In accordance with the respiratory-based protocol 120 of FIG. 6, once each respiration threshold(s) is no longer being exceeded, the medical procedure may be reinitiated. However, the medical procedure could resume on any appropriate basis, such as after the expiration of a predetermined amount of time from the identification of a first condition.

Another embodiment of a respiration evaluation protocol that may be utilized by the protocol 120 of FIG. 6 to execute the patient respiration data evaluation associated with its steps 132 and 140 is illustrated in FIG. 9 and is identified by reference numeral 188. The respiratory-based control protocol 120 of FIG. 6 provides for the display of patient respiration data through its step 136, as previously noted. The respiration evaluation protocol 188 of FIG. 9 includes this display functionality in relation to its patient respiration data assessment (and which thereby may replace the display step 136 of the protocol 120 of FIG. 6).

The respiration evaluation protocol 188 of FIG. 9 accommodates categorizing patient respiration data through its evaluation, and which may be used determine the manner in which patient respiration data is displayed. In this regard, the protocol 188 determines if the patient respiration data that is currently being evaluated is within one of three ranges, and this determination may be made in any order (e.g., the first determination may be whether the patient respiration data is within the third range, versus the first range). Any appropriate number of ranges may be utilized by the protocol 188 (e.g., two or more). Each such respiration range may encompass any appropriate range of respiration values. Generally and for purposes of the display function of the respiration evaluation protocol 188 of FIG. 9, each respiration range is displayed in a different color to visually present at least one indication of the patient's current respiration level.

Step 192 of the protocol 188 determines if the patient respiration data is within a first range. In one embodiment and as will be discussed below in relation to FIGS. 10A-C, the first range corresponds with patient respiration data that is within 0% to ±75% of the corresponding respiration threshold, and which may be equated with a "normal" respiration. If the patient respiration data currently being evaluated is within the first range, the protocol 188 proceeds to step 196 and which results in the current patient respiration data being displayed in a first color (e.g., green), as well as for a continuance of the medical procedure through step 218.

Step 200 of the protocol 188 determines if the patient respiration data is within a second range. In one embodiment, the second range corresponds with patient respiration data that is between ±75% and ±100% of the corresponding respiration threshold, and which may be equated with a "cautionary" respiration zone that is between a "normal" respiration zone and respiration levels that have been associated with a sudden respiratory event or a first condition. If the patient respiration data currently being evaluated is within the second range, the protocol 188 proceeds from step 200 to step 204 and which results in the current patient respiration data being displayed in a second color (e.g., yellow), as well as for a continuance of the medical procedure through step 218.

Patient respiration data that falls outside of each of the first and second ranges is equated with a sudden respiratory event (e.g., at least ±100% of the corresponding respiration threshold, and which equates with a first condition) for purposes of the respiration evaluation protocol 188 and as indicated by step 208. The protocol 188 proceeds to step 212 in this case and results in the current patient respiration data being displayed in a third color (e.g., red). Other appropriate indications of this first condition may be presented as well (e.g., the entire respiration meter 220 of FIGS. 10A-C may flash). Moreover and as noted above, the medical procedure may be suspended in this instance in any appropriate manner, for instance through execution of step 216 of the protocol 188. In accordance with the respiratory-based protocol 120 of FIG. 6, once the patient respiration data is no longer within the third range, the medical procedure may be re-initiated or otherwise as discussed herein.

Figure 10A:
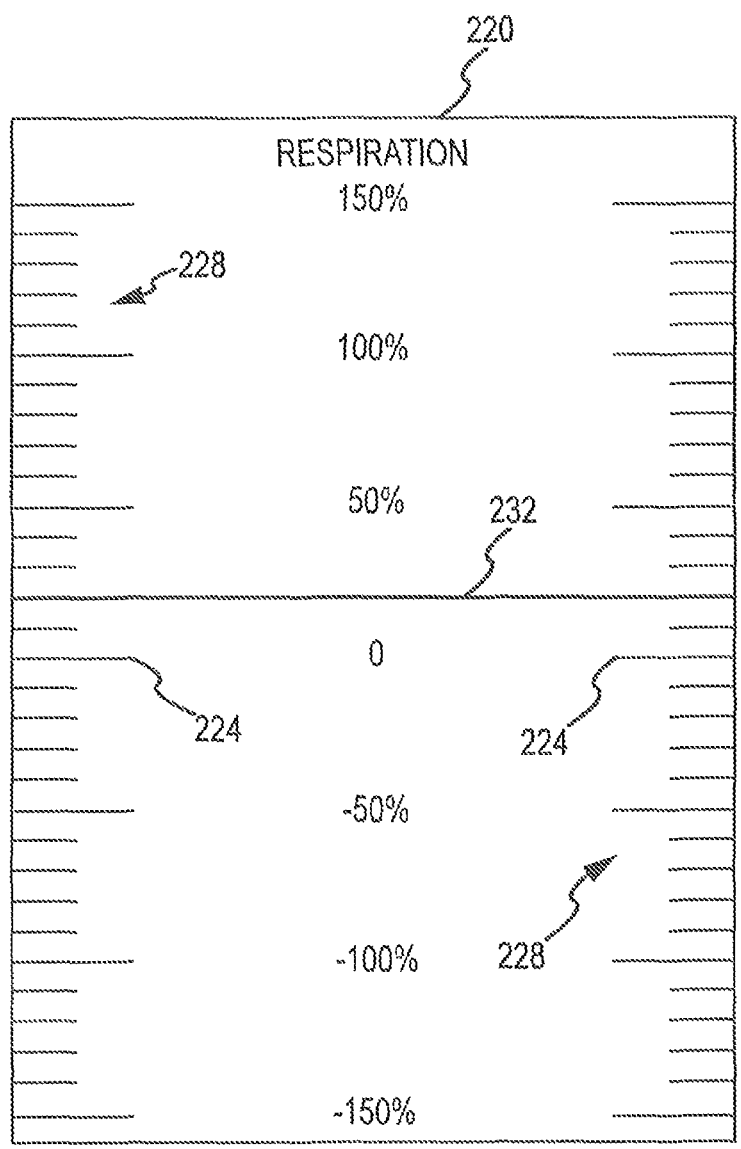
FIG. 10A is one embodiment of a visual output that may be used by the respiratory-based control protocol of FIG. 6 to present patient respiratory data, illustrating a patient respiration level within a first range.
Figure 10B:
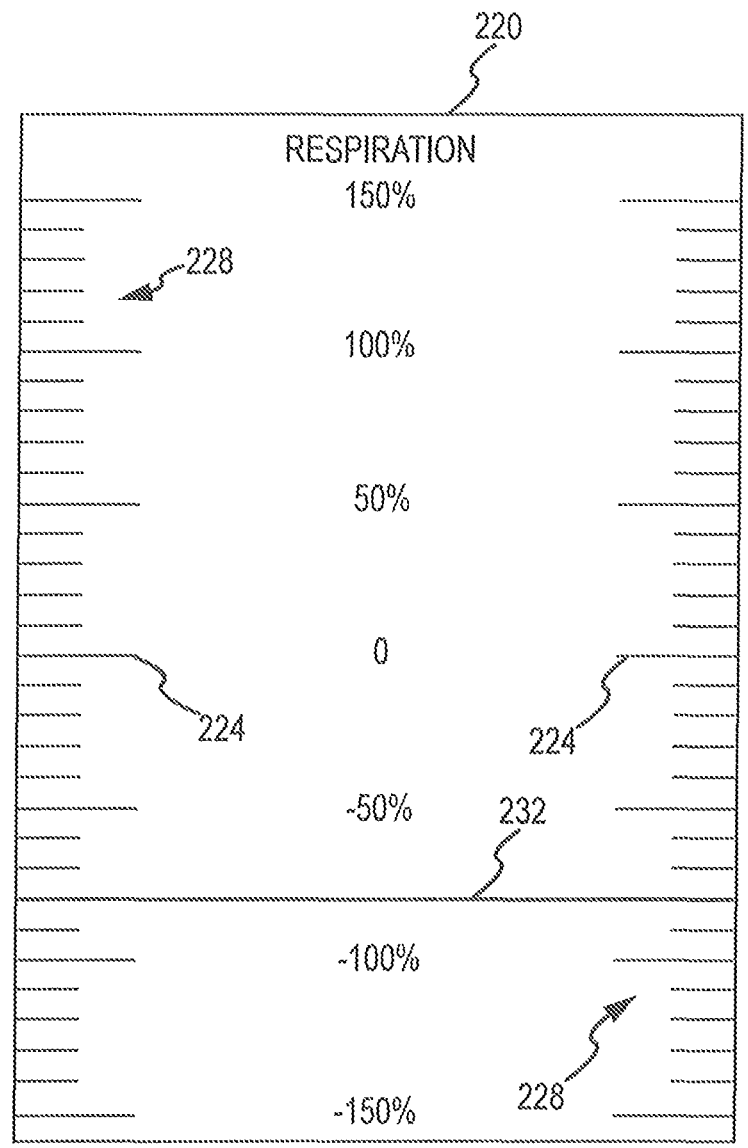
FIG. 10B is one embodiment of a visual output that may be used by the respiratory-based control protocol of FIG. 6 to present patient respiratory data, illustrating a patient respiration level within a second range.
Figure 10C:
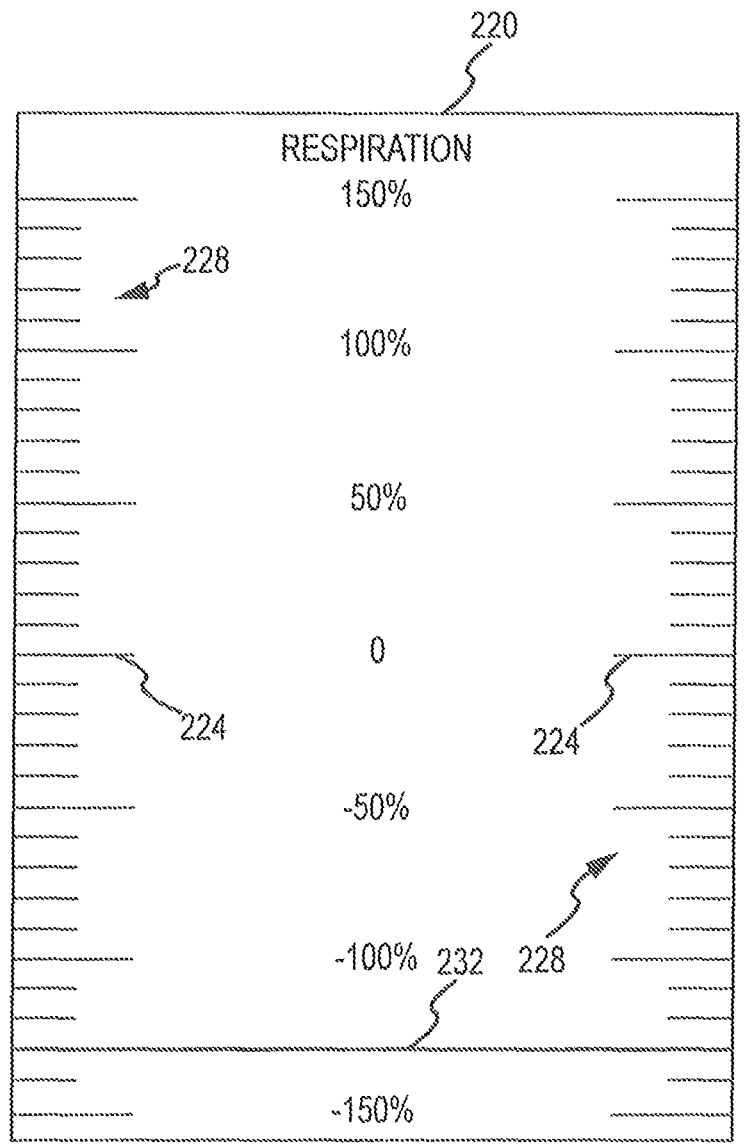
FIG. 10C is one embodiment of a visual output that may be used by the respiratory-based control protocol of FIG. 6 to present patient respiratory data, illustrating a patient respiration level within a third range.

FIGS. 10A-C present representative displays that accommodate use of the respiration evaluation protocol 188 of FIG. 9. The displays of FIGS. 10A-C are each in the form of a respiration meter 220 that includes gradations 228, a datum 224 that occupies the "0" position on the meter 220 (although this does not mean that the associated respiration value is in fact "0" at this time), and a movable indicator bar 232. The indicator bar 232 moves during a patient's respiratory cycle and to a magnitude that corresponds with the patient's current respiration level. That is, the indicator bar 232 rises and falls on the respiration meter 220 in accordance with the changing of patient's respiration level during the respiration cycle.

The respiration meter 220 expresses the patient's respiration as a percentage of two respiration thresholds—what may be characterized as a maximum respiration threshold and a minimum respiration threshold, and each of which may be of any appropriate value and determined on any appropriate basis. For instance, a maximum respiration value or an average maximum respiration value may be determined from a patient respiratory data sample, and which may be used to define or establish one respiration baseline. A corresponding respiration threshold may then be set or established from this respiration baseline and which may be of any appropriate value. Although the maximum respiration threshold could be set equal to the maximum respiration baseline, in one embodiment the maximum respiration threshold is greater/less than the maximum respiration baseline by a certain amount. Similarly a minimum respiration value or an average minimum respiration value may be determined from a patient respiratory sample, and which may be used to define or establish another respiratory baseline. A corresponding respiration threshold may then be set or established from this respiration baseline and which may be of any appropriate value. Although the minimum respiration threshold could be set equal to the minimum respiration baseline, in one embodiment the minimum respiration threshold is greater/less than the minimum respiration baseline by a certain amount.

The maximum respiration threshold (+100% in the illustrated embodiment) may correspond with the end of patient inhalation, while the minimum respiration threshold (−100% in the illustrated embodiment) may correspond with the end of a patient exhalation, although the reverse could be utilized as well. Both the maximum respiration threshold and the minimum respiration threshold are referenced to a common datum 224. Although this datum is illustrated as having a value of 0%, this does not necessarily mean that the value of the patient respiration data corresponding with the datum 224 is in fact "0," although such could be the case. For instance, the datum 224 could be any appropriate value. In one embodiment, patient respiration data on the "plus" side of the respiration meter 220 corresponds with respiration levels on one side of a reference line associated with a waveform embodying patient respiration data, while patient respiration data on the "minus" side of the respiration meter 220 correspond with respiration levels on the opposite side of this same reference line.

Although the absolute value of the maximum respiration threshold value could be the same as the absolute value of the minimum respiration threshold value, such need not be the case. Stated another way, the differential value between the datum 224 and each of the maximum and minimum respiration thresholds may or may not be the same. In any case, when current patient respiration data is being evaluated by the respiration evaluation protocol 188 of FIG. 9 and when using the respiration meter 220 of FIGS. 10A-C, the value of the current patient respiration data could be divided by the value associated with the relevant one of the maximum respiration threshold and the minimum respiration threshold. If the values of the maximum and minimum thresholds were the same, obviously only one value would need to be utilized. The respiration threshold that should be used as the denominator in relation to the current respiration data evaluation could be determined on any appropriate basis. For instance, the maximum respiration threshold could be used if the value of the current patient respiration data was within a certain range, while the minimum respiration threshold could be used if the value of the current patient data was within another range. Another option would be to use the maximum respiration threshold if the patent respiration data was on one side of a reference line associated with a waveform embodying the patient respiration data, and to use the minimum respiration threshold if the patient respiration data was on the opposite side of this same reference line (e.g., if the patient respiration data was being presented by a waveform for the first condition analysis).

FIG. 10A is a representative position of the indicator bar 232 within the first range and in accordance with the above-noted embodiment. Therefore, the indicator bar 232 would be presented in a first color. FIG. 10B is a representative position of the indicator bar 232 within the second range and in accordance with the above-noted embodiment. Therefore, the indicator bar 232 would be presented in a second color. Finally, FIG. 10C is a representative position of the indicator bar 232 within the third range and in accordance with the above-noted embodiment. Therefore, the indicator bar 232 would be presented in a third color. In addition to or in alternative to a color, other indicators may be used, such as shape or sound.

The respiration assessment system 112 may be used for any appropriate application. For instance, it may be desirable to incorporate the respiration assessment system 112 into the navigation/visualization system 5 of FIG. 1 and as previously noted. The same display that presents navigation/visualization data could provide patient respiratory assessment data, or this data could be presented in side-by-side relation to each other on separated displays, or at least on displays that are proximate to each other. The respiration assessment system 112 could be used with a navigation/visualization system that does not include any respiration compensation functionality, as well as with a navigation/visualization system that does incorporate appropriate respiration compensation functionality.

Respiration compensation functionality is available in the Ensite™ Advanced Mapping System by St. Jude Medical, Inc., and is addressed by the above-noted U.S. Pat. No. 7,263,397, which is hereby incorporated by reference. Generally, respiration compensation functionality attempts to minimize the respiration artifact from cardiac models and mapping. That is, during patient respiration the heart and any electrodes positioned therein will move relative to the various patch electrodes that are positioned on the patient's skin at any appropriate location. The surface electrode impedance is monitored in relation to a respiratory data sample that is taken of at least one patient respiration cycle that does not include any sudden respiratory event. As the impedance changes at the surface electrodes, the respiration compensation functionality adapts the impedance output based upon the initial respiratory data sample to adaptively compensate for motion artifacts.

The above-noted type of respiration compensation functionality thereby shows the heart and any endocardial electrode without any (or with only minimal) respiratory motion. The respiration assessment system 112 could be used in this type of system configuration. In this regard, it may be desirable to present those gradations 228 in the respiration compensation zone in a different color than the remaining gradations 228, although this is optional. The respiration assessment system 112 could also be used without any respiration compensation functionality at all, where the navigation/visualization system would then display the heart and any endocardial electrodes with respiratory motion. The respiration assessment system 112 may also be used other than with navigation/visualization systems.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A respiratory assessment system, comprising:
   a cardiac navigation and/or visualization system having a processor and a display;
   at least one sensor operatively connected to said cardiac navigation and/or visualization system, wherein an output from said at least one sensor is indicative of a patient respiration; and
   respiration assessment logic operatively connected to said at least one sensor and configured to:
   identify an existence of a sudden respiratory event, and
   automatically suspend a cardiac medical procedure upon said respiration assessment logic identifying an existence of said sudden respiratory event.

2. The respiratory assessment system of claim 1, wherein said at least one sensor comprises an electrode that is disposable on a skin of a patient.

3. The respiratory assessment system of claim 1, wherein said output from said at least one sensor comprises electrophysiological data.

4. The respiratory assessment system of claim 1, wherein said sudden respiratory event is representative of a current patient respiration that is outside of a predetermined respiration range.

5. The respiratory assessment system of claim 4, wherein said predetermined respiration range is adjustable.

6. The respiratory assessment system of claim 1, wherein said sudden respiratory event is representative of a current patient respiration that exceeds at least one respiration threshold.

7. The respiratory assessment system of claim 1, wherein the respiration assessment logic identifies the existence of the sudden respiratory event and suspends the cardiac medical procedure.

8. The respiratory assessment system of claim 1, wherein said respiration assessment logic evaluates impedance data for an existence of said sudden respiratory event.

9. The respiratory assessment system of claim 1, wherein said respiration assessment logic evaluates an amplitude of impedance data for an existence of said sudden respiratory event.

10. The respiratory assessment system of claim 1, wherein said cardiac medical procedure comprises marking a physiological location.

11. The respiratory assessment system of claim 1, wherein said cardiac medical procedure is selected from the group consisting of cardiac labeling, cardiac geometry collection, cardiac mapping, and cardiac lesion marking.

12. The respiratory assessment system of claim 1, wherein said display outputs current patient respiration data.

13. The respiratory assessment system of claim 1, wherein said sudden respiratory event is when a current patient respiration is outside of a predetermined respiration range, wherein a representation of current patient respiration data on said display is in a first color when said current patient respiration data is within a first portion of said predetermined respiration range, and wherein a representation of said current patient respiration data on said display is in a second color when said current patient respiration data is within a second portion of said predetermined respiration range that is entirely outside of said first portion of said predetermined respiration range.

14. A method for performing a cardiac medical procedure, comprising the steps of:
   executing a cardiac medical procedure using a cardiac navigation and/or visualization system having a processor and a display;
   acquiring in the processor current patient respiration data based on output from at least one sensor that is indicative of patient respiration;
   evaluating in the processor said current patient respiration data to identify whether a sudden respiratory event exists; and
   automatically suspending execution of said cardiac medical procedure if said evaluating step identifies a sudden respiratory event.

15. The method of claim 14, wherein said cardiac medical procedure comprises providing an electrophysiological function or combination of functions.

16. The method of claim 14, wherein said cardiac medical procedure comprises marking a physiological location of a patient's heart.

17. The method of claim 14, wherein said cardiac medical procedure is selected from the group consisting of cardiac labeling, cardiac geometry collection, cardiac mapping, and cardiac lesion marking.

18. The method of claim 14, wherein said acquiring step comprises acquiring electrophysiological data.

19. The method of claim 14, wherein said evaluating step comprises comparing said current patient respiration data with at least one predetermined respiration value.

20. The method of claim 14, further comprising an initializing step that is executed before initiating said evaluating step, wherein data acquired by said initializing step is thereafter used by said evaluating step.

21. The method of claim 20, wherein said initializing step comprises acquiring a patient respiration data sample that includes at least one patient respiration cycle, and thereafter determining at least one respiration threshold from said patient respiration data sample.

22. The method of claim 14, further comprising an initializing step that is executed before initiating said evaluating step, wherein said initializing step comprises acquiring a first patient respiration data sample that includes at least one patient respiration cycle and that is thereafter used by said evaluating step, wherein said method further comprises acquiring a second patient respiration data sample in response to an output of said evaluating step, wherein said second patient respiration data sample includes at least one patient respiration cycle and that is thereafter used by said evaluating step versus said first patient respiration data sample.

23. A method for performing a cardiac medical procedure comprising the steps of:
- acquiring a first patient respiration data sample based on output from at least one sensor that is indicative of patient respiration, wherein said first patient respiration data sample includes at least one patient respiration cycle;
- marking a plurality of physiological locations within a patient's heart using at least one electrophysiology catheter in conjunction with cardiac navigation and/or visualization system;
- acquiring current patient respiration data based on output from at least one sensor that is indicative of patient respiration;
- evaluating said current patient respiration data in relation to said first patient respiration data sample to identify whether a sudden respiratory event exists; and
- automatically suspending execution of said marking step if said evaluating step identifies a sudden respiratory event.

* * * * *